United States Patent
Hart

(10) Patent No.: US 8,308,638 B2
(45) Date of Patent: Nov. 13, 2012

(54) INTERNAL TISSUE RETRACTOR

(75) Inventor: Charles C. Hart, Summerville, SC (US)

(73) Assignee: Applied Medical Resources Corporation, Rancho Santa Margarita, CA (US)

( * ) Notice: Subject to any disclaimer, the term of this patent is extended or adjusted under 35 U.S.C. 154(b) by 584 days.

(21) Appl. No.: 12/467,839

(22) Filed: May 18, 2009

(65) Prior Publication Data

US 2009/0227844 A1 Sep. 10, 2009

Related U.S. Application Data

(63) Continuation of application No. 10/539,641, filed as application No. PCT/US2004/001584 on Jan. 20, 2004, now abandoned.

(60) Provisional application No. 60/442,390, filed on Jan. 24, 2003.

(51) Int. Cl.
*A61B 1/32* (2006.01)

(52) U.S. Cl. ...................................................... 600/206

(58) Field of Classification Search .................. 600/184, 600/201, 203, 206, 208–210, 235; 128/830–834, 128/837; 623/1.5, 1.51, 2.14, 2.18
See application file for complete search history.

(56) References Cited

U.S. PATENT DOCUMENTS

| | | | |
|---|---|---|---|
| 1,275,520 A | 8/1918 | Bell | |
| 1,624,276 A | 4/1927 | Nelson | |
| 1,947,649 A | 12/1931 | Kadavy | |
| 1,949,863 A | 3/1934 | Hay | |
| 3,882,855 A | 5/1975 | Schulte et al. | |
| 4,190,042 A | 2/1980 | Sinnreich | |
| 4,428,375 A | 1/1984 | Ellman | |
| 4,497,317 A | 2/1985 | Boschetti | |
| 4,889,107 A | 12/1989 | Kaufman | |
| 5,080,088 A | 1/1992 | LeVahn | |
| 5,143,082 A | 9/1992 | Kindberg et al. | |
| 5,161,806 A | 11/1992 | Baisells | |
| 5,163,949 A | 11/1992 | Bonutti | |
| 5,333,624 A | 8/1994 | Tovey | |

(Continued)

FOREIGN PATENT DOCUMENTS

WO WO 91/14392 10/1991

OTHER PUBLICATIONS

European Patent Office, Supplementary Partial European Search Report for European Patent Application No. 04 703698.3, dated Jun. 23, 2008.

(Continued)

*Primary Examiner* — Anu Ramana
(74) *Attorney, Agent, or Firm* — John F. Heal

(57) ABSTRACT

A positionable internal retraction device is provided comprising a malleable ring member and a web-like structure. The retraction device operates to temporarily reposition tissues and organs from an operative site to provide a clear access and visual path for the surgeon. The ring member may be elongated, twisted, folded, bent or deformed to provide an appropriate insertion profile and subsequent functional shape. The retraction device may be shaped for both open and minimally invasive surgeries. The retraction device is atraumatic and may be used for retraction of delicate tissues and organs. The ring member may have different bending biases. The web-like structure may be constructed of any elastic material that can stretch and recover from the shaping and reshaping of the ring member.

23 Claims, 11 Drawing Sheets

U.S. PATENT DOCUMENTS

| | | | |
|---|---|---|---|
| 5,366,460 A * | 11/1994 | Eberbach | 606/151 |
| 5,370,650 A | 12/1994 | Tovey et al. | |
| 5,439,476 A | 8/1995 | Frantzides | |
| 5,582,577 A | 12/1996 | Lund et al. | |
| 5,651,762 A | 7/1997 | Bridges | |
| 5,656,012 A | 8/1997 | Sienkiewicz | |
| 5,803,902 A | 9/1998 | Sienkiewicz et al. | |
| 5,865,728 A | 2/1999 | Moll et al. | |
| 5,899,942 A | 5/1999 | Berman | |
| 5,947,895 A | 9/1999 | Warner | |
| 6,077,281 A * | 6/2000 | Das | 606/151 |
| 6,155,972 A | 12/2000 | Nauertz et al. | |
| 6,216,698 B1 | 4/2001 | Regula | |
| 6,264,604 B1 | 7/2001 | Kieturakis et al. | |
| 6,293,906 B1 | 9/2001 | Vanden Hoek et al. | |
| 6,416,459 B1 | 7/2002 | Haindl | |
| 6,416,554 B1 | 7/2002 | Alfreness et al. | |
| 6,425,856 B1 | 7/2002 | Shapland et al. | |
| 6,450,983 B1 | 9/2002 | Rambo | |
| 6,482,146 B1 | 11/2002 | Alferness et al. | |
| 6,958,037 B2 | 10/2005 | Ewers et al. | |
| 6,998,165 B2 | 2/2006 | Howland | |
| 7,452,371 B2 * | 11/2008 | Pavcnik et al. | 623/1.24 |
| 2002/0045800 A1 | 4/2002 | Lau et al. | |
| 2002/0133055 A1 | 9/2002 | Haindl | |
| 2003/0181974 A1 * | 9/2003 | Xie et al. | 623/1.24 |

OTHER PUBLICATIONS

Co-Pending U.S. Appl. No. 10/539,641, filed Jun. 16, 2005, entitled "Internal Tissue Retractor".

* cited by examiner

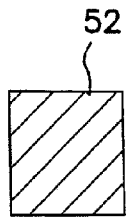
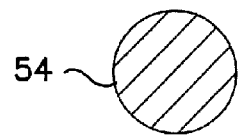
FIG. 14  FIG. 15  FIG. 16
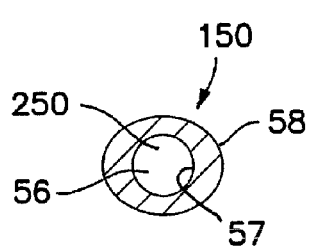
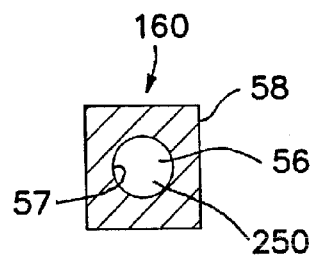
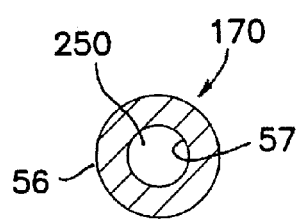
FIG. 17  FIG. 18  FIG. 19
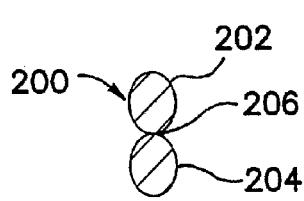
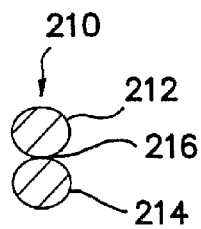
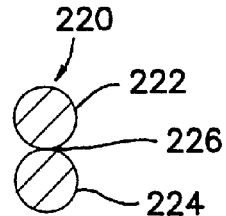
FIG. 20  FIG. 21  FIG. 22

INTERNAL TISSUE RETRACTOR

CROSS-REFERENCE TO RELATED APPLICATIONS

This application is a continuation of U.S. patent application Ser. No. 10/539,641 entitled "INTERNAL TISSUE RETRACTOR," filed on Jun. 16, 2005, which is a national stage filing under 35 U.S.C. §371 of International Application No. PCT/US2004/001584 entitled "INTERNAL TISSUE RETRACTOR," filed on Jan. 20, 2004, which claims the benefit of U.S. Provisional Patent Application No. 60/442,390, entitled "INTERNAL TISSUE RETRACTOR," filed on Jan. 24, 2003. The entire disclosures of these applications are each hereby incorporated by reference as if set forth in full herein.

BACKGROUND OF THE INVENTION

1. Field of the Invention

The present invention generally relates to surgical retractors and, in particular, to a retractor for retracting tissues and organs to facilitate access and viewing during a surgical procedure.

2. Discussion of the Prior Art

Surgical procedures often require temporary retraction of surrounding tissues and organs from the immediate surgical site to provide an access and viewing path for the surgeon. In the prior art, clamps, towels and other makeshift methods have been used to separate and hold structures in a preferred position away from the point of surgery. Retractors have been developed to push and hold tissues and organs away from the surgical site. These devices typically include paddles and/or collapsible fingers that expand after the retractors have been inserted into the body. The retractors may include expandable frames for supporting expandable sheaths or covers. While some of these devices have been successfully used for smaller tissues and organs, the current retractors have had difficulty in clearing the surgical field of larger and more slippery tissues and organs. In particular, the shape, size and fragility of the tissues and organs may present problems during surgery. For example, large, soft organs such as the intestines and/or stomach are often more difficult to retract and hold in place than from harder, less slippery tissues such as the muscles.

Another drawback of the current retraction devices is they typically need to be attached to an external device to provide support and/or manipulation. These devices often need to be over-tightened or compressed to maintain a proper grip and position on the tissues and organs, which may cause damage to delicate tissues and organs. Moreover, a large surgical incision must be made to accommodate all the components of the retraction device. As a result, the surgical site may become cluttered and encumbered by the many additional components of the retraction device. Therefore, there is a need in the art for a retraction device that can be flexibly utilized to clear a surgical site of tissues and organs having different shapes, sizes and fragility. The retraction device should be atraumatic and be able to twist, fold or bend to facilitate insertion and removal.

SUMMARY OF THE INVENTION

The present invention is directed to a positionable internal retraction device providing an operable area while holding adjacent structures in a desired position. The retraction device comprises a malleable ring member that supports a web-like structure. The ring member may be elongated, twisted, folded, bent or deformed to provide an appropriate insertion profile and subsequent functional shape. The retraction device may be shaped for both open and minimally invasive surgeries. The retraction device is atraumatic and may be used for retraction of delicate tissues and organs. The ring member may have different cross-sectional construction providing different bending biases. The ring member may include a lumen sized and configured to receive a reinforcement member providing a desired bending bias in a preferred plane. The reinforcement member may comprise a "shape memory" material that enables the reinforcement member to return to its desired shape or condition after being bent.

The web-like structure is constructed of an elastic material such as a bias-woven or knitted fabric that can stretch and recover from the shaping and reshaping of the ring member. The web-like structure operates to retain the body tissues and organs of different shapes and sizes. More particularly, the web-like structure is able to retain both hard and soft body tissues and organs during surgery. It is preferable that the web-like structure is a transparent membrane.

In another aspect of the invention, the ring member further comprises an internal lumen defining a wall, which may be of any geometric shape providing a desired bending bias. The ring member may further comprise a reinforcement member placed within the lumen to provide additional bending bias. The reinforcement member may be formed of a plastic component, a metallic component or any combination thereof. The metallic component includes at least one of aluminum, titanium, stainless steel and Nitenol. In the above aspect of the invention, the reinforcement member may be placed in some sections of the ring member to keep these sections substantially straight. It is appreciated that each of the ring member, the reinforcement member and the internal wall may have a cross-section or profile of any geometric shape to provide a desired bending bias in a preferred plane. In yet another aspect of the invention, the ring member further comprises a second lumen and a second reinforcement member placed within the second lumen to provide a desired bending bias.

DESCRIPTION OF THE DRAWINGS

FIG. 14 illustrates a cross-section view of a ring member having an oval shape;

FIG. 15 illustrates a cross-section view of a ring member having a square shape;

FIG. 16 illustrates a cross-section view of a ring member having a circular shape;

FIG. 17 illustrates a cross-section view of a ring member having an oval shape and an internal lumen;

FIG. 18 illustrates a cross-section view of a ring member having a square shape and an internal lumen;

FIG. 19 illustrates a cross-section view of a ring member having a circular shape and an internal lumen;

FIG. 20 illustrates a cross-section view of a ring member having a pair of vertical ovals connected along the long axes;

FIG. 21 illustrates a cross-section view of a ring member having a pair of vertical ovals connected along the short axes;

FIG. 22 illustrates a cross-section view of a ring member having a connected pair of circles;

DESCRIPTION OF PREFERRED EMBODIMENTS AND BEST MODE OF THE INVENTION

Figures 1A, 1B:
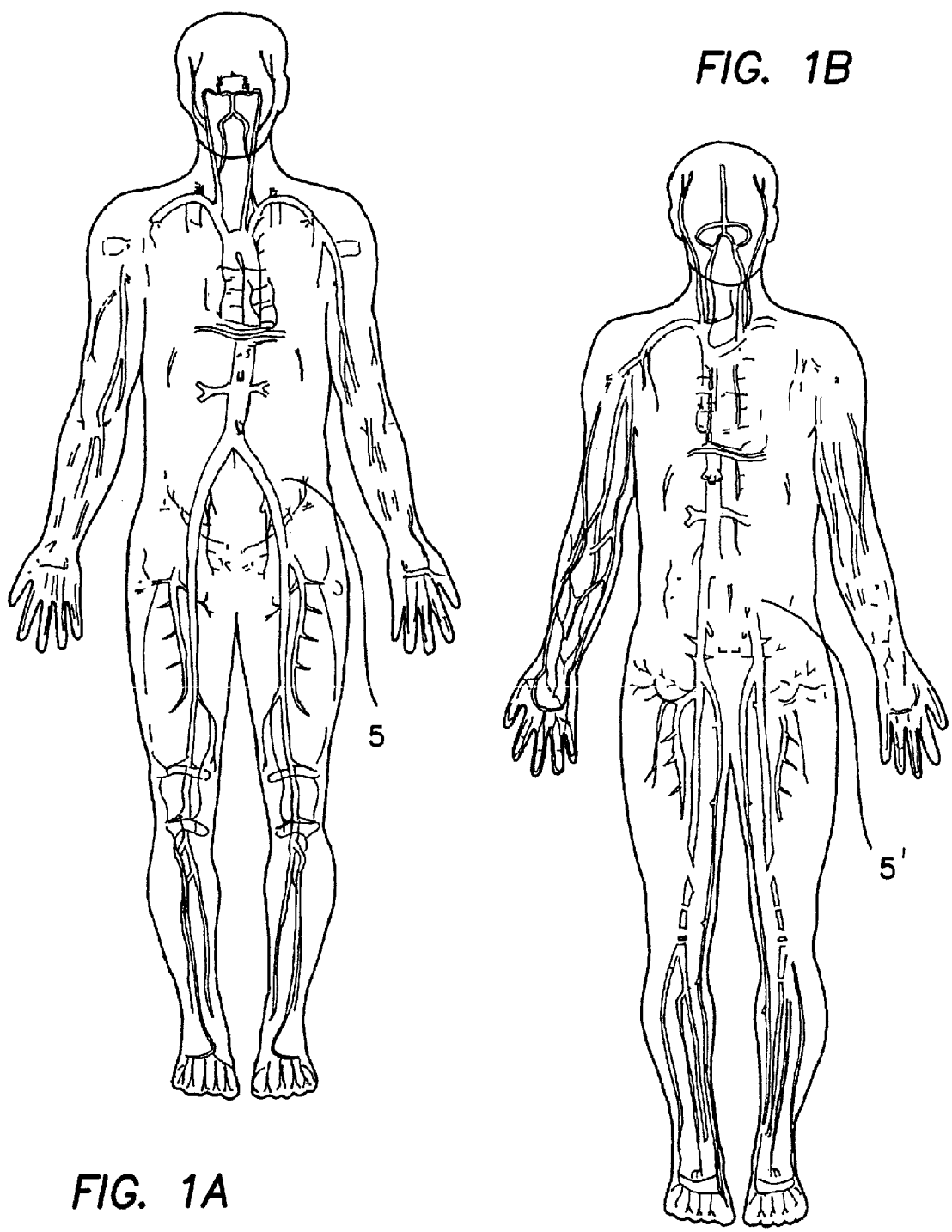
FIGS. 1(a) and 1(b) illustrate the arterial and venous systems, respectively, of a human being.
Figure 2:
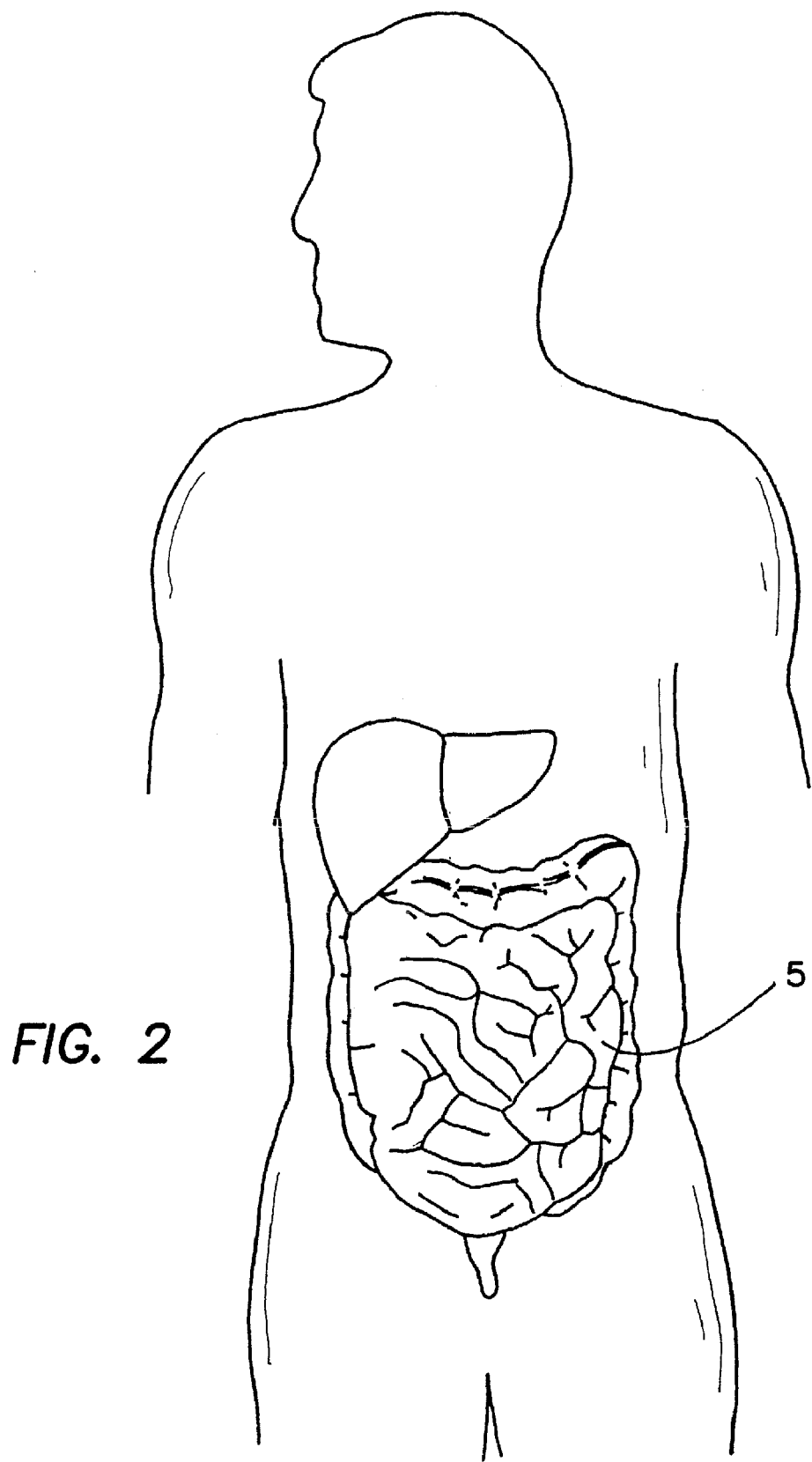
FIG. 2 illustrates an abdominal region of a human being that may have to be retracted during a surgical procedure.
Figure 3:
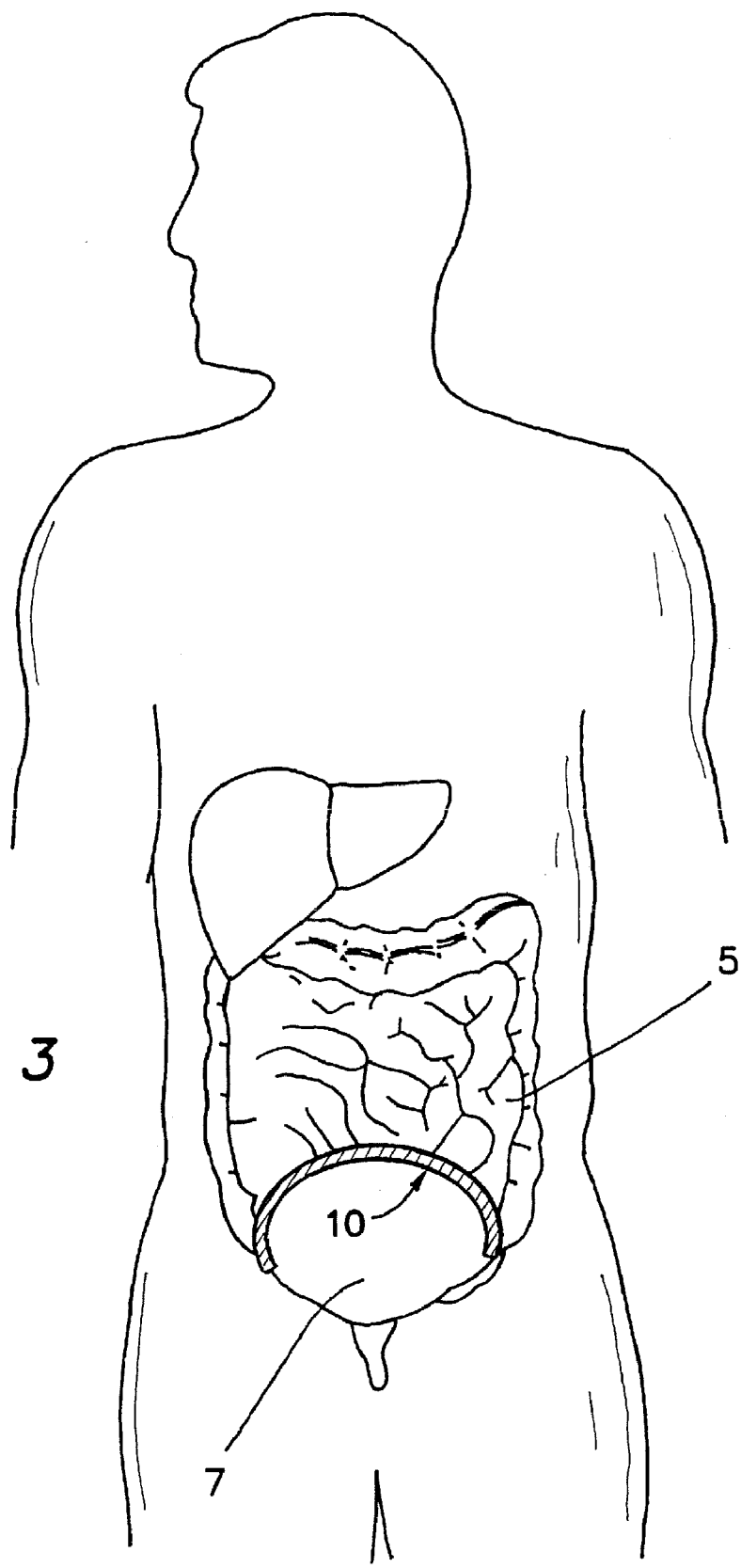
FIG. 3 illustrates a retraction device of the present invention positioned to relocate a portion of the intestines.

Surgical procedures often require that tissues and organs be temporarily repositioned to provide a clear visual path for the surgeon. For example, FIGS. 1(a) and 1(b) illustrate the arterial and venous systems, respectively, of a human being that is often covered or obscured by body tissues and/or organs that may need to be repositioned during a surgical procedure. The obscuring tissues and/or organs may be the abdominal content such as the intestines, bowel, fat, etc., as illustrated in FIG. 2, which may need to be relocated and held in a preferred position away from the point of surgery. FIG. 3 illustrates a retraction device 10 of the present invention that may be placed in a surgical area such as the abdominal area to provide an unobstructed workplace 7. The retraction device 10 operates to retract or reposition abdominal content 5 away from the immediate workplace 7. Once the retraction device 10 is properly placed in the abdominal area, the surgeon will have a clear and reasonably unobstructed view of the operative site.

Figure 4:
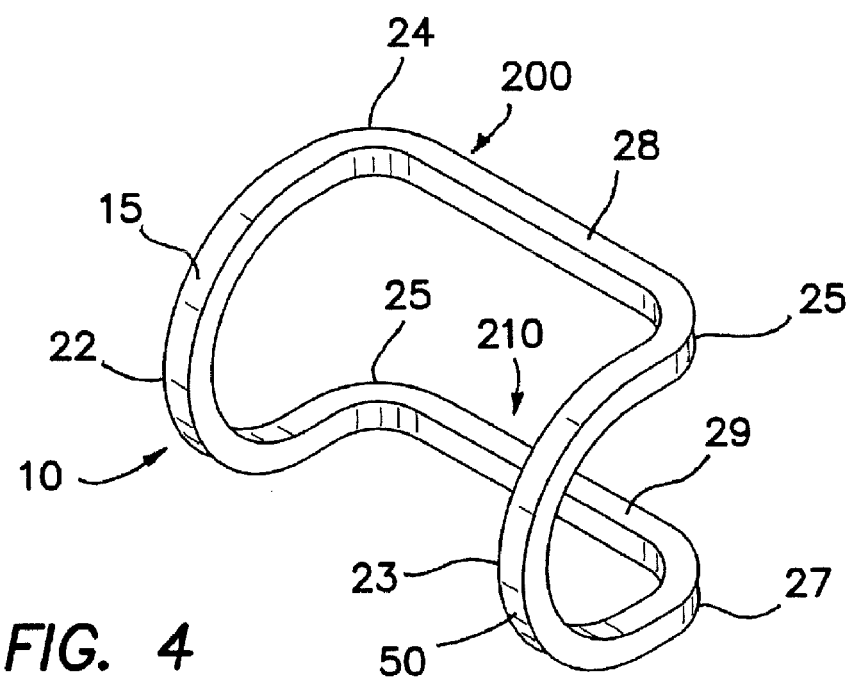
FIG. 4 illustrates a ring member of a retraction device of the present invention formed in a first condition.
Figure 5:
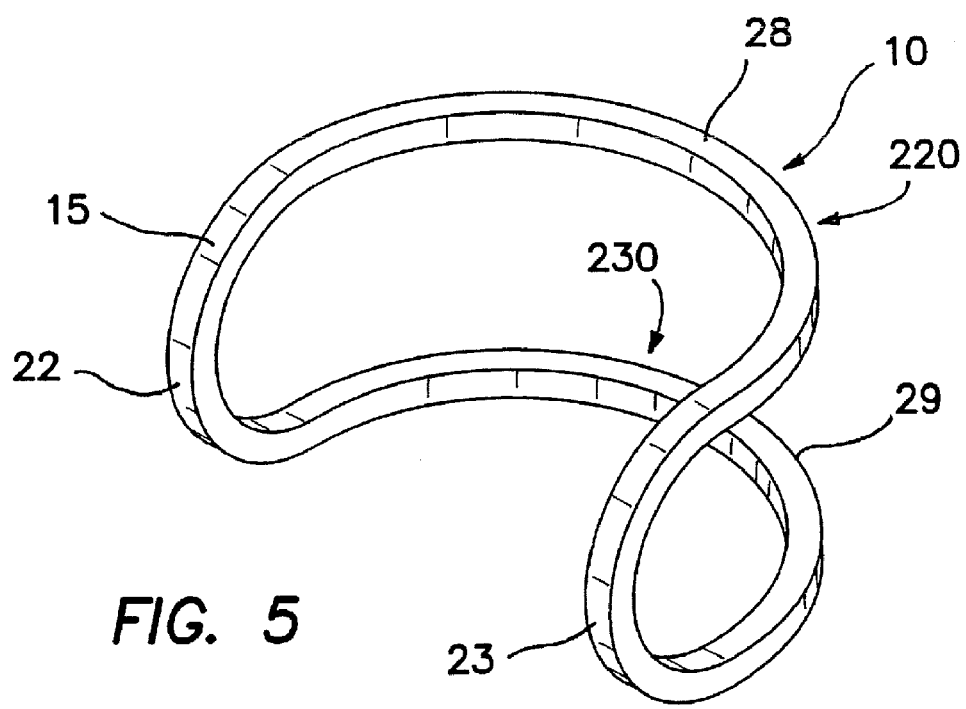
FIG. 5 illustrates a ring member of a retraction device of the present invention formed in a second condition.

Referring to FIGS. 4 and 5, the retraction device 10 of the present invention comprises a ring member or wire element 15 that is made of a malleable material. That is, the ring member 15 is bendable and will stay bent in the shape or form in which it is bent. The ring member 15 may include first bending portions 22, 23 and second bending portions 24, 25, 26 and 27. The first bending portions 22, 23 may be used to fold the ring member 15 in half bringing opposing portions 28, 29 toward each other as illustrated in FIG. 5. Once the ring member 15 is folded in half along the first bending portions 22, 23, the second bending portions 24, 25, 26 and 27 may then be bent to form substantially straight portions 200, 210 as illustrated in FIG. 4. It is appreciated that the ring member 15 may have a plurality of bending portions and may be bent in any shape depending on the needs of each particular surgical procedure.

Figure 6:
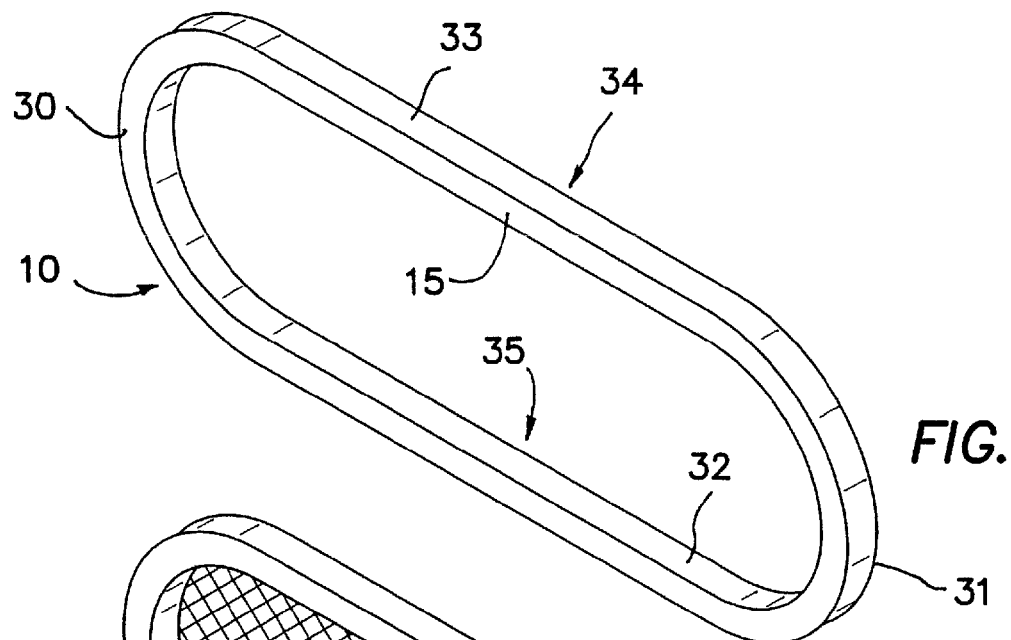
FIG. 6 illustrates a perspective view of a ring member of a retraction device of the present invention formed in accordance with another embodiment of the invention.
Figure 7:
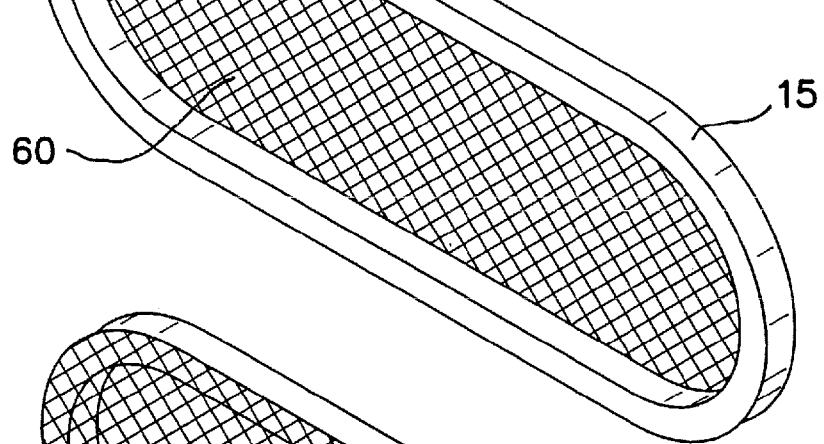
FIG. 7 illustrates a perspective view of a ring member of a retraction device having a web structure formed on a back side of the ring member.
Figure 8:
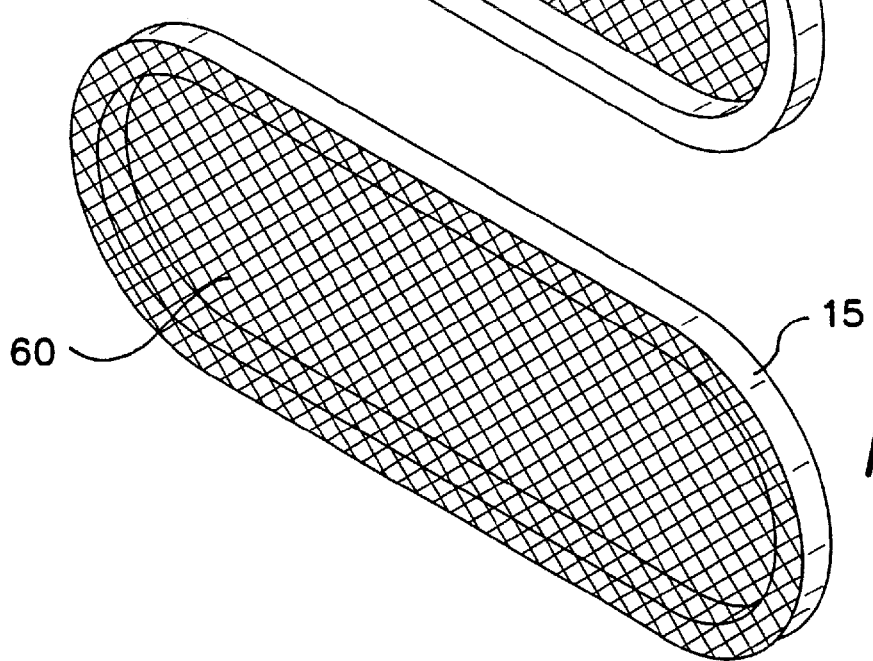
FIG. 8 illustrates a perspective view of a ring member of a retraction device having a web structure formed on a front side of the ring member.

Referring to FIGS. 6-8, the ring member 15 of the retraction device 10 is illustrated in a flat, low profile condition that is suitable for insertion into a surgical incision. The ring member 15 has a front ring surface 30, a back ring surface 31, an inner ring surface 32, and an outer ring surface 33. The ring member 15 further includes substantially parallel portions 34, 35 that may be squeezed together forming the low profile condition. The ring member 15 may support a membrane or web structure 60 such as a fabric cover that is fixedly attached to the front ring surface 30 as illustrated in FIG. 8, the back ring surface 31 as illustrated in FIG. 7, or to both the front and back ring surfaces 30 and 31. It is foreseeable that the membrane 60 may be fixedly attached to at least one of the inner ring surface 32 and the outer ring surface 33.

The membrane or web structure 60 is preferably flexible such that it can retain tissues and organs of different shapes and sizes. Furthermore, the membrane or web structure 60 should be able to retain both hard and soft tissues such as the muscles and bowel during abdominal surgery. Specifically, the retraction device 10 and membrane 60 should be taught enough to securely hold and separate hard tissues and organs and, at the same time, be flexible enough to gently retain soft tissues and organs so as not to damage the tissues and organs or affect their circulation. The membrane 60 is preferably transparent so that tissues and organs are viewable through the membrane. An advantage of this feature is it allows a surgeon to view and ascertain the condition of a tissue or organ during a surgical procedure.

Figure 9:
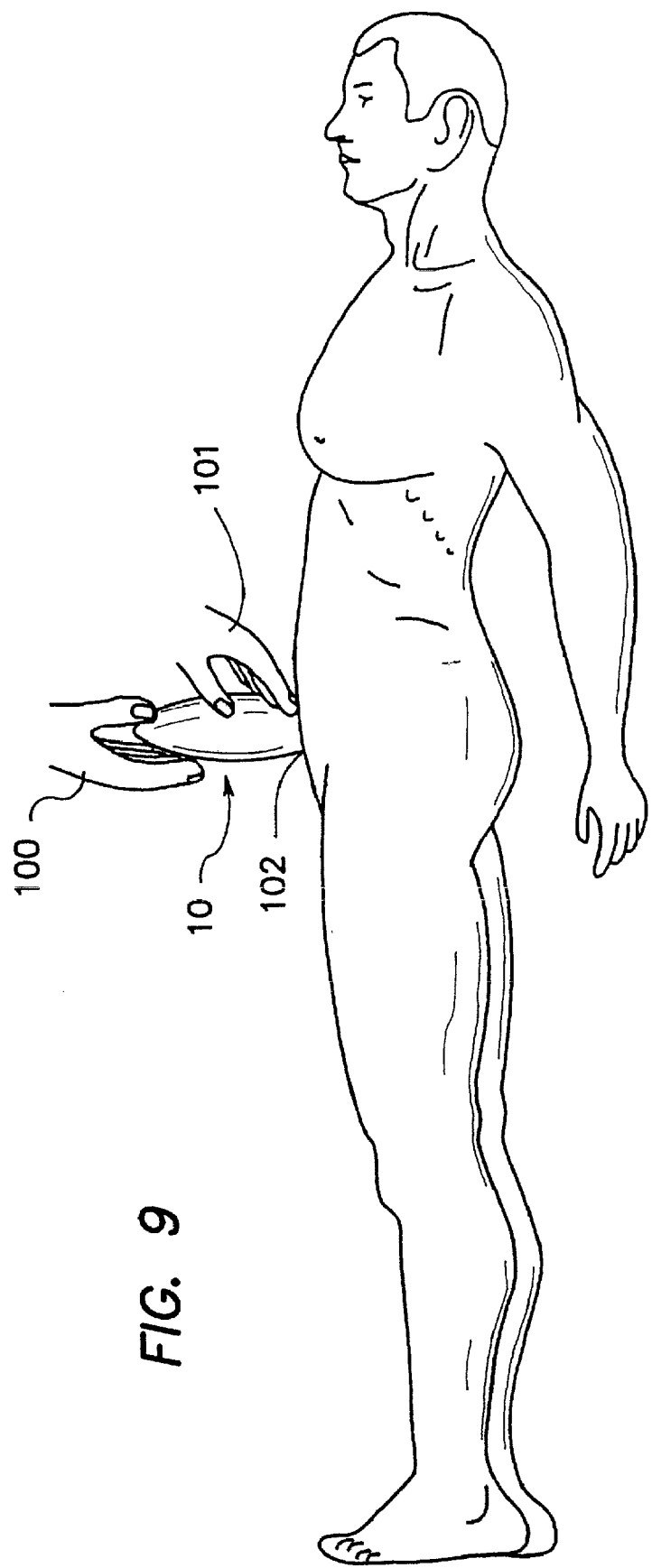
FIGS. 9-11 illustrate the steps of inserting a retraction device of the present invention into an abdominal region of a human body.
Figure 10:
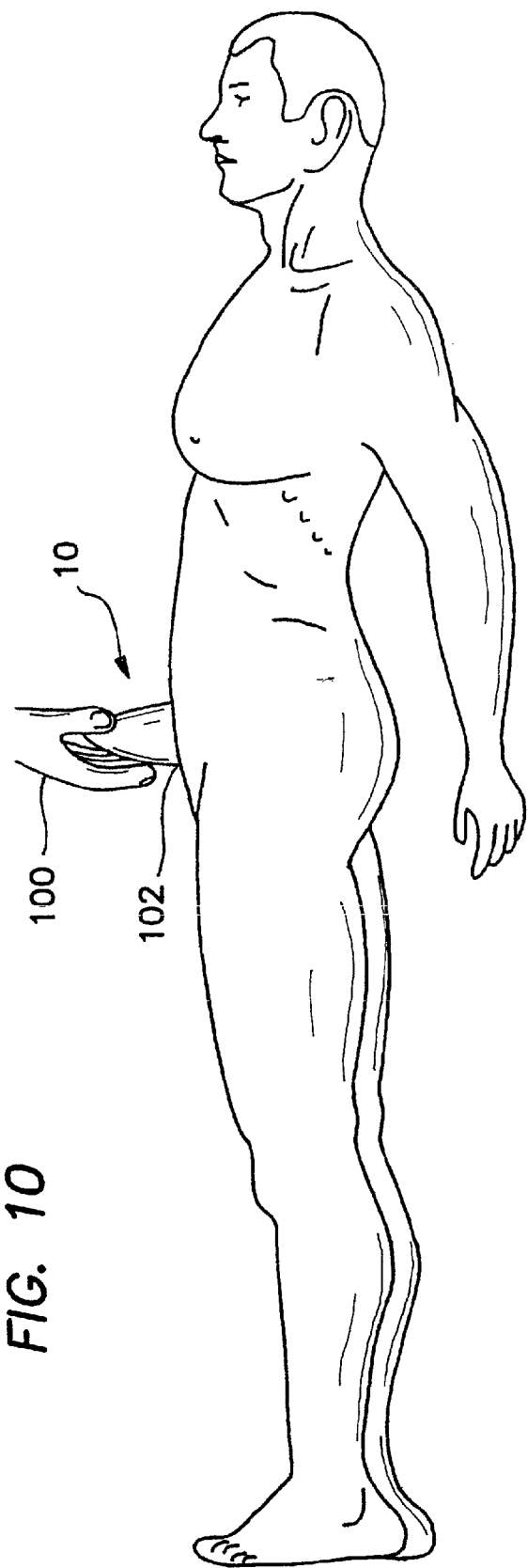
Figure 11:
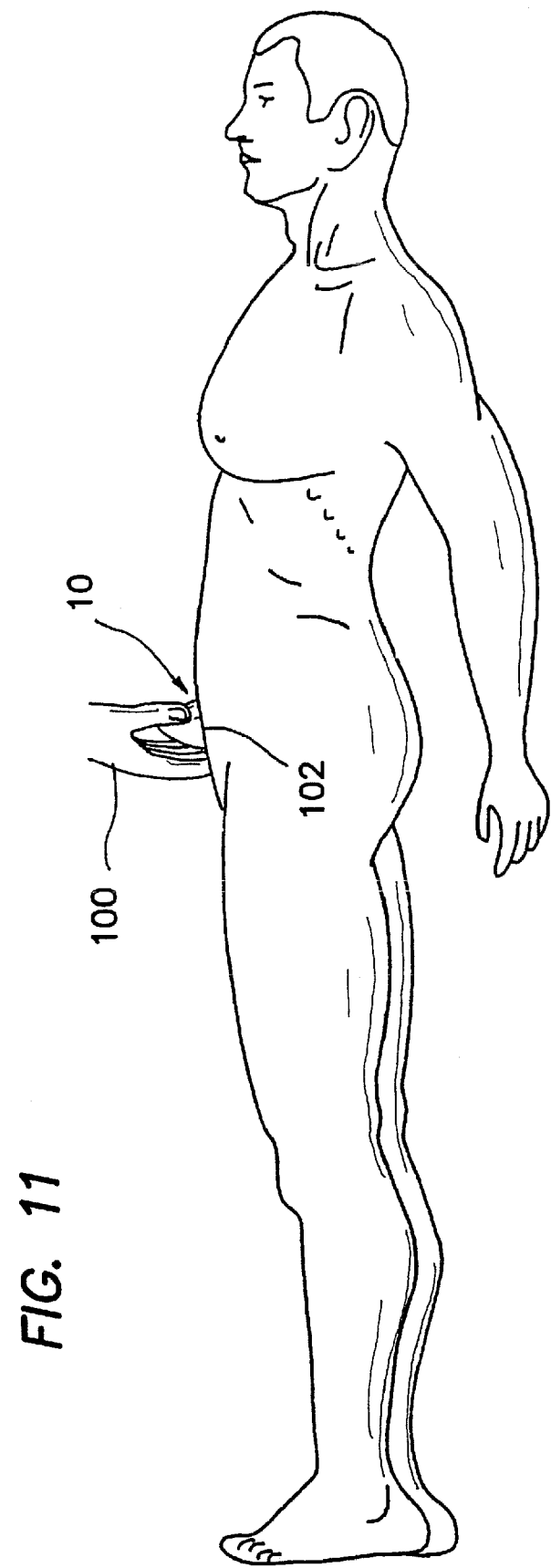
Figure 12:
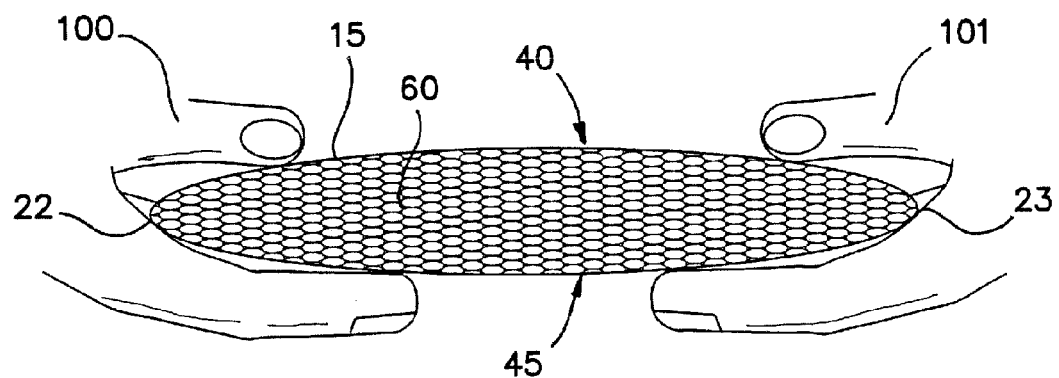
FIG. 12 illustrates a retraction device of the present invention having a knitted web member as it is being held prior to insertion into a surgical incision of a body.
Figure 13:
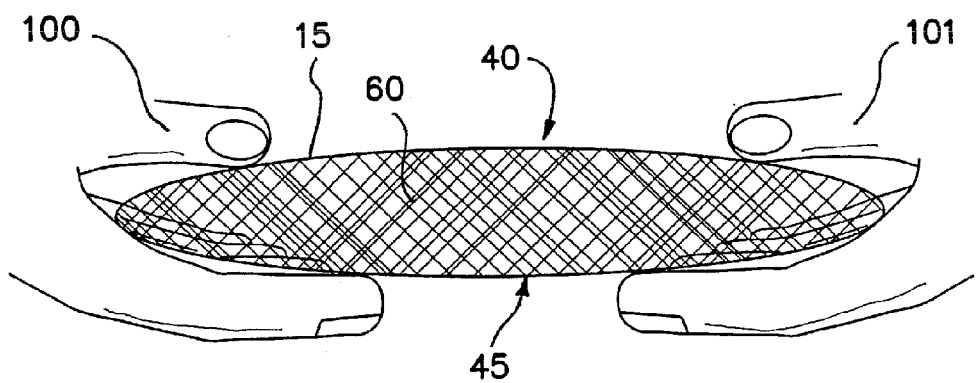
FIG. 13 illustrates a retraction device of the present invention having a woven web member as it is being held prior to insertion into a surgical incision of a body.

Once the retraction device 10 is flattened, it may be inserted into a surgical incision 102 as generally illustrated in FIGS. 9-11. The retraction device 10 may be inserted through the small incision 102 because it is flattened and the retraction device 10 does not fully expand to its final shape until it is partially or fully inserted to a point well within the abdominal cavity. As illustrated in FIGS. 12 and 13, the retraction device 10 may be flattened by squeezing along sides 40, 45 of the ring member 15 in a first condition to facilitate insertion. It is appreciated that the membrane 60 is also sized and configured to stretch and recover in response to the shaping and reshaping of the ring member 15. The membrane 60 may be a bias-woven or knitted fabric that exhibits elastic properties. Alternatively, the membrane 60 may be constructed of any elastic material that responds to the shaping and reshaping of the ring member 15.

The ring member may have different cross-sectional shapes and configurations as illustrated in FIGS. 14-22. Each of the cross-sectional shapes of the ring member provides a bending bias in a preferred plane. For instance, the ring member of FIG. 14 has an oval shape 50 providing a preference for bending along the long axis over bending along the short axis. That is, a retraction device having an oval ring member will be easier to bend and shape along the long axis than along the short axis. In addition, the region bent along the long axis is more resilient than the region bent along the short axis. As a result, the strongest retraction for this configuration is developed in that portion which comprises a bend along the long axis. In another embodiment of the invention, FIG. 15 illustrates a cross-section view of a ring member having a substantially square shape 52 that bends equally in two planes but resists bending diagonally. An additional embodiment may also include a ring member having a rectangular cross-section that provides preferential bending in one plane and increased resistance to bending in the opposite plane. The rectangular cross-section would also substantially resist bending diagonally.

FIG. 16 illustrates a ring member having a circular cross-section 54 where the entire ring member may bend equally in all directions and that yields only to the forces applied by the membrane 60. The circular cross-section 54 is therefore shapeable to a greater degree in all directions than other geometries and may allow the retraction device to be placed in awkward positions or to be shaped in a manner that avoids delicate or sensitive structures. It is appreciated that the ring member may have a cross-section of any shape or geometry to provide a desired bending bias in a preferred plane.

Figure 23:
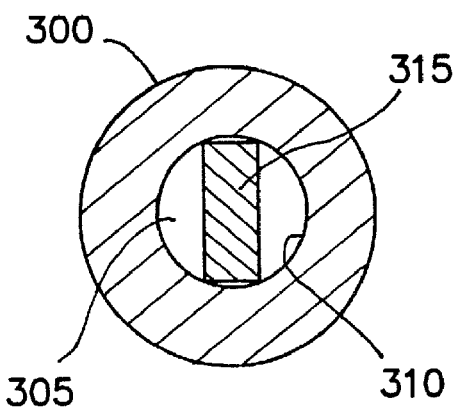
FIG. 23 illustrates a cross-section view of a circular ring member having a lumen and a reinforcement member placed therein.

Referring to FIGS. 17-19, each of the ring members of FIGS. 14-16, respectively, may include an internal lumen 56 defining a wall 57. The wall 57 may be circular or form a shape that provides a desired bending bias. That is, the lumen 56 may impart a bending bias in a similar manner as the various cross-sections of the ring members discussed above. The relationship between the wall 57 of the lumen 56 and a surface 58 of the ring member may also impact the bending bias. For example, the thickness of the wall 57, i.e., the distance between the wall 57 and the surface 58 of the ring member, may determine a bending bias. In another embodiment of the invention, a reinforcement member 315 is placed within a lumen 305 to provide additional bending bias as illustrated in FIG. 23. The reinforcement member 315 may comprise a plastic component, a metal component or any combination thereof. The metal component may include aluminum, titanium, stainless steel or any combination of these compounds.

The reinforcement member 315 may be inserted and placed in a preferred location along the lumen 305 so that a preferred bending bias is developed in specific regions along the lumen 305 of the ring member. For instance, referring back to FIGS. 4 and 5, a preferred embodiment may require that a section or sections 28, 29 of the retraction device 10 be substantially straight whereas sections 24, 25, 26 and 27 are bendable. In this case, a rigid reinforcement member may be placed along the sections 28, 29 to keep these sections substantially straight. A second, more resilient reinforcement member may then be placed adjacent to the first, more rigid reinforcement member within the lumen to prevent the first reinforcement member from shifting position along the lumen.

In yet another embodiment of the invention, the reinforcement member 315 comprises a material having a "shape memory" that enables the reinforcement member to return to its desired shape. With this design, the reinforcement member may be used with a retraction device that can be severely deformed during insertion while maintaining the ability to return to its original shape or condition. The shape memory materials, for example, include a blend of nickel and titanium metals, which are also commonly referred to as Nitenol®. In particular, a retraction device would be constructed with a reinforcement member comprising Nitenol®, or the like, in a preferred shape and condition, the retraction device would then be subjected to cold temperature so that it becomes malleable or flexible. During use, the retraction device would be bent to facilitate insertion into a preferred location. Once inserted, the reinforcement member would warm to body temperature and return to the preferred shape and condition, thereby returning the retraction device to its original shape and condition. An advantage of the reinforcement member of the invention is it allows the ring member to be severely deformed, even beyond the normal elastic limits of the material from which the ring member is constructed.

Moreover, the reinforcement member has very good resistance to kinking and permanent deformation because it is constructed of, e.g., nickel-titanium alloys. That is, with this construction, the reinforcement member of the invention placed within the lumen of the ring member can prevent the ring member from being overstressed or kinked. In addition, the reinforcement member may allow the retraction device to be compressed or folded or otherwise reshaped into a condition that allows it to be inserted into a body cavity through the smallest possible surgical incision.

FIGS. 20-22 illustrate ring members 200, 210 and 220, respectively, comprising a plurality of cords in accordance with additional embodiments of the invention. The cords of ring members 200, 210 and 220 may be constructed according to previously discussed geometric cross-sectional shapes or profiles. FIG. 20 illustrates the ring member 200 comprising a pair of oval cords 202, 204 that are vertically joined at point 206 along the long axes of the cords 202, 204. FIG. 21 illustrates the ring member 210 comprising a pair of oval cords 212, 214 that are vertically joined at point 216 along the short axes of the cords 212, 214. In yet another embodiment of the invention, FIG. 22 illustrates the ring member 220 comprising a pair of circular cords 222, 224 joined at point 226 along the length of each of the cords 222, 224. Each of the ring members 200, 210 and 220 exhibits bending preferences in accordance with the individual cord geometries combined with the overall geometry of the connected cords.

In each of the above embodiments, the ring members were formed by combining two cords; however, it is appreciated that a plurality of cord elements comprising three or more individual cords may be combined to exhibit a desired bending preference. It is further noted that each of the above constructions may be achieved by extrusion of material having a cross-section that resembles a combination of cords or by the actual connection of individual cord elements. In addition, the combined cords may be contained within the lumen of a covering tube or wrap.

As discussed above, FIG. 23 illustrates a cross-section view of a ring member 300 having an internal lumen 305 and a reinforcement member 315 placed within the lumen 305. The lumen 305 defines a wall 310. In this embodiment, the reinforcement member 315 has a cross-sectional shape or profile that is different from the cross-sectional shape or profile of the ring member 300. For example, the ring member 300 may have a circular cross-section while the reinforcement member 315 may have a rectangular cross-section. With a different cross-sectional shape or profile, the reinforcement member 315 may impart a different bending bias on the ring member 300. It is appreciated that the ring member 300, reinforcement member 315 and wall 310 may have different cross-sectional shapes or profiles from one another to provide a desired bending bias in a preferred plane.

Figure 24:
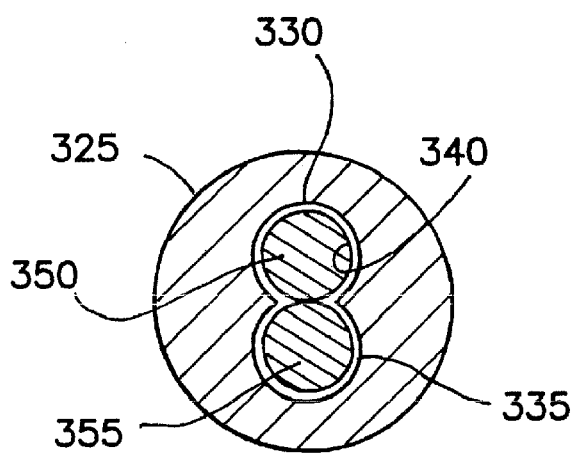
FIG. 24 illustrates a cross-section view of a circular ring member having a plurality of lumens and reinforcement members placed within the lumens.
Figure 25:
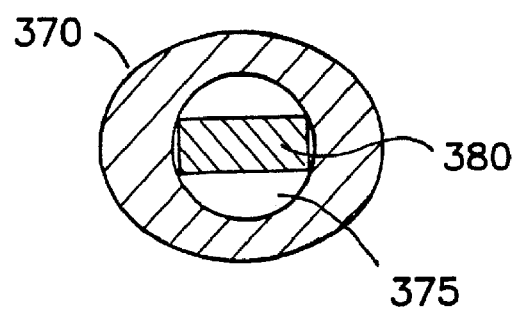
FIG. 25 illustrates a cross-section view of an oval ring member having a lumen and a biasing reinforcement member placed within the lumen.

FIG. 24 illustrates a ring member 325 having a plurality of internal lumens 330, 335 that may or may not communicate with one another in accordance with another embodiment of the invention. The ring member 325 further includes reinforcement members 350, 355 that may be inserted into the lumens 330, 335, respectively, to provide a desired bending bias of a retraction device. In another embodiment of the invention, FIG. 25 illustrates a ring member 370 having an oval cross section, a round or oval lumen 375, and a rectangular reinforcement member 380 placed within the lumen 375. The configuration of ring member 370 provides a bending bias that allows the retraction device to be shaped or bent in a preferred plane while providing great strength in an opposite plane.

Many alterations and modifications may be made by those having ordinary skill in the art without departing from the spirit and scope of the invention. Therefore, it must be understood that the illustrated embodiments have been set forth only for the purposes of examples and that they should not be taken as limiting the invention.

The invention claimed is:

1. A method for temporarily repositioning tissue in a surgical procedure comprising:
   inserting a temporary tissue repositioning device through an incision into a body cavity, the temporary tissue repositioning device comprising:
      a bendable frame comprising:
         a first axis and a second axis intersecting the first axis;
         a surface defined by the first axis and the second axis;
         a first side and a second side defined by the surface;
         a plurality of elongate first bending portions parallel to the first axis and parallel to each other; and
         a plurality of second bending portions, operatively coupled to the first bending portions; and
      a fabric cover disposed over the first side of the frame, the fabric cover adapted to retain tissue and the fabric cover defining a tissue retention surface,
   wherein
      the bendable frame is reversibly and manually bendable between a first state and a second state;
      in the first state, the bendable frame is flattened such that the tissue retention surface is generally planar;
      in the second state, the bendable frame is bent into a nonplanar configuration such that the tissue retention surface is nonplanar;
      the frame in the first state remains in the first state;
      the frame in the second state remains in the second state; and
      the fabric cover disposed over the first side conforms to the surface in the first state and the second state;
   wherein inserting the temporary tissue repositioning device through the incision into the body cavity comprises inserting the temporary tissue repositioning device through the incision into an abdominal cavity;
   deforming the repositioning device into the second state; and
   repositioning tissue away from a surgical workplace.

2. The method of claim 1, wherein the first bending portions of the temporary tissue repositioning device are longer than the second bending portions.

3. The method of claim 1, wherein the first bending portions and the second bending portions of the temporary tissue repositioning device comprise wire.

4. The method of claim 1, wherein the first bending portions and the second bending portions of the temporary tissue repositioning device comprise at least one of aluminum, titanium, stainless steel, a shape memory material, and nickel-titanium alloy.

5. The method of claim 1, wherein the frame of the temporary tissue repositioning device comprises a ring comprising the plurality of first bending portions and the plurality of second bending portions.

6. The method of claim 1, wherein the fabric cover of the temporary tissue repositioning device is woven or knit.

7. The method of claim 1, wherein the fabric cover of the temporary tissue repositioning device extends over the second side of the frame.

8. The method of claim 1, wherein in the second state, the frame of the temporary tissue repositioning device is bent along the first axis.

9. The method of claim 1, wherein in the second state, the frame of the temporary tissue repositioning device is bent along the second axis.

10. The method of claim 1, wherein inserting the temporary tissue repositioning device through an incision comprises inserting the temporary tissue repositioning device in the first state.

11. The method of claim 1, wherein repositioning tissue comprises repositioning an organ.

12. The method of claim 1, wherein inserting the temporary tissue repositioning device through an incision into a body cavity comprises inserting the temporary tissue repositioning device fully into the body cavity.

13. A method for temporarily repositioning tissue in a surgical procedure comprising:
   inserting a temporary tissue repositioning device through an incision into a body cavity, the temporary tissue repositioning device comprising:
      a bendable frame comprising:
         a first axis and a second axis intersecting the first axis;
         a surface defined by the first axis and the second axis;
         a first side and a second side defined by the surface;
         a plurality of elongate first bending portions parallel to the first axis and parallel to each other; and
         a plurality of second bending portions, operatively coupled to the first bending portions; and
      a fabric cover disposed over the first side of the frame, the fabric cover adapted to retain tissue and the fabric cover defining a tissue retention surface,
   wherein
      the bendable frame is reversibly and manually bendable between a first state and a second state;
      in the first state, the bendable frame is flattened such that the tissue retention surface is generally planar;
      in the second state, the bendable frame is bent into a nonplanar configuration such that the tissue retention surface is nonplanar;
      the frame in the first state remains in the first state;
      the frame in the second state remains in the second state; and
      the fabric cover disposed over the first side conforms to the surface in the first state and the second state;
   deforming the repositioning device into the second state; and
   repositioning tissue away from a surgical workplace, wherein repositioning tissue comprises repositioning an organ.

14. The method of claim 13, wherein inserting the temporary tissue repositioning device through an incision comprises inserting the temporary tissue repositioning device in the first state.

15. The method of claim 13, wherein inserting the temporary tissue repositioning device through an incision into a body cavity comprises inserting the temporary tissue repositioning device fully into the body cavity.

16. The method of claim 13, wherein the first bending portions of the temporary tissue repositioning device are longer than the second bending portions.

17. The method of claim 13, wherein the first bending portions and the second bending portions of the temporary tissue repositioning device comprise wire.

18. The method of claim 13, wherein the first bending portions and the second bending portions of the temporary tissue repositioning device comprise at least one of aluminum, titanium, stainless steel, a shape memory material, and nickel-titanium alloy.

19. The method of claim 13, wherein the frame of the temporary tissue repositioning device comprises a ring comprising the plurality of first bending portions and the plurality of second bending portions.

20. The method of claim 13, wherein the fabric cover of the temporary tissue repositioning device is woven or knit.

21. The method of claim 13, wherein the fabric cover of the temporary tissue repositioning device extends over the second side of the frame.

22. The method of claim 13, wherein in the second state, the frame of the temporary tissue repositioning device is bent along the first axis.

23. The method of claim 13, wherein in the second state, the frame of the temporary tissue repositioning device is bent along the second axis.

* * * * *